(12) United States Patent
Kelly (10) Patent No.: US 11,559,200 B2
(45) Date of Patent: Jan. 24, 2023

(54) METHOD AND APPARATUS FOR MEASURING A PROPERTY OF AN EYE

(71) Applicant: The University of Manchester, Manchester (GB)

(72) Inventor: Jeremiah Michael Francis Kelly, Stockport (GB)

(73) Assignee: The University of Manchester, Manchester (GB)

( * ) Notice: Subject to any disclaimer, the term of this patent is extended or adjusted under 35 U.S.C. 154(b) by 474 days.

(21) Appl. No.: 16/629,292

(22) PCT Filed: Jul. 9, 2018

(86) PCT No.: PCT/GB2018/051938
§ 371 (c)(1),
(2) Date: Jan. 7, 2020

(87) PCT Pub. No.: WO2019/008395
PCT Pub. Date: Jan. 10, 2019

(65) Prior Publication Data
US 2020/0221945 A1 Jul. 16, 2020

(30) Foreign Application Priority Data
Jul. 7, 2017 (GB) ..................................... 1710991

(51) Int. Cl.
*G06K 9/00* (2022.01)
*A61B 3/06* (2006.01)
(Continued)

(52) U.S. Cl.
CPC ............ *A61B 3/063* (2013.01); *A61B 3/0025* (2013.01); *A61B 5/7246* (2013.01); *G16H 50/20* (2018.01); *G16H 50/30* (2018.01)

(58) Field of Classification Search
CPC ...... A61B 3/063; A61B 3/0025; A61B 5/7246; A61B 3/0033; G16H 50/20; G16H 50/30
See application file for complete search history.

(56) References Cited

U.S. PATENT DOCUMENTS

| 2007/0121071 A1* | 5/2007 | Jackson | ............... | A61B 3/0025 |
| | | | | 351/246 |
| 2010/0168606 A1* | 7/2010 | Edwards | ............... | A61B 3/0033 |
| | | | | 600/558 |
| 2018/0271362 A1* | 9/2018 | Palczewski | ............ | A61B 3/024 |

FOREIGN PATENT DOCUMENTS

| WO | 2005/023094 A2 | 3/2005 |
| WO | 2008/100613 A2 | 8/2008 |

(Continued)

OTHER PUBLICATIONS

Owsley et al., "Cone- and Rod-Mediated Dark Adaptation Impairment in age-Related Maculopathy," *Ophthalmology* 774:1728-1735, 2007.

(Continued)

*Primary Examiner* — Shervin K Nakhjavan
(74) *Attorney, Agent, or Firm* — Seed Intellectual Property Law Group LLP (57) ABSTRACT

Embodiments of the present invention provide a computer-implemented method of determining a parameter indicative of dark adaptation of an eye, comprising receiving threshold data from a dark adaptometer indicative of a perception threshold of the eye, fitting first and second models to the threshold data, wherein the first model is associated with a first dark adaptation mechanism and the second model is associated with the first dark adaption mechanism and a second dark adaptation mechanism, determining a confidence associated with the fitting of each of the first and second models to the received threshold data, iteratively repeating the steps of receiving the threshold data and fitting (Continued)

the first and second models in dependence on the determined confidence, and outputting an indication of one or more parameters indicative of dark adaptation of an eye associated with one or both of the first and second models.

11 Claims, 4 Drawing Sheets

(51) Int. Cl.
    *G16H 50/30*     (2018.01)
    *G16H 50/20*     (2018.01)
    *A61B 3/00*     (2006.01)
    *A61B 5/00*     (2006.01)

(56) References Cited

FOREIGN PATENT DOCUMENTS

| WO | 2012/022938 A1 | 2/2012 |
|---|---|---|
| WO | 2017/095910 A1 | 6/2017 |

OTHER PUBLICATIONS

International Search Report and Written Opinion dated Sep. 26, 2018, for International Application No. PCT/GB2018/051938, 15 pages.

Murray et al., "New Rapid Digital Dark Adaptometer that Shows High Sensitivity and Specificity for Early AMD." Invest. Ophthalmol. Vis. Sci. 57(12), p. 3705. Abstract published Sep. 2016 [online], Acessed on Jan. 11, 2018.

Kelly, "Isolating Rod Function in the Human Eye", PhD Thesis, University of Manchester, published 2012, Accessed Jan. 11, 2018.

McGwin et al., "Using Nonlinear Regression to Estimate Parameters of Dark Adaptation", Behavior Research Methods, Istruments, & Computers, vol. 31(4), pp. 712-717, published Dec. 1999, Accessed on Jan. 11, 2018.

European Search Report, Application No. GB1710991.9, Jan. 16, 2018, 5 pages.

International Preliminary Report on Patentability and Written Opinion of the International Searching Authority dated Jan. 7, 2020, for International Application No. PCT/GB2018/051938, 8 pages.

\* cited by examiner

METHOD AND APPARATUS FOR MEASURING A PROPERTY OF AN EYE

BACKGROUND

The present invention relates to a method and apparatus for measuring a property of an eye of a subject, and in particular to a property of a retina of that eye of the subject.

Figure 1:
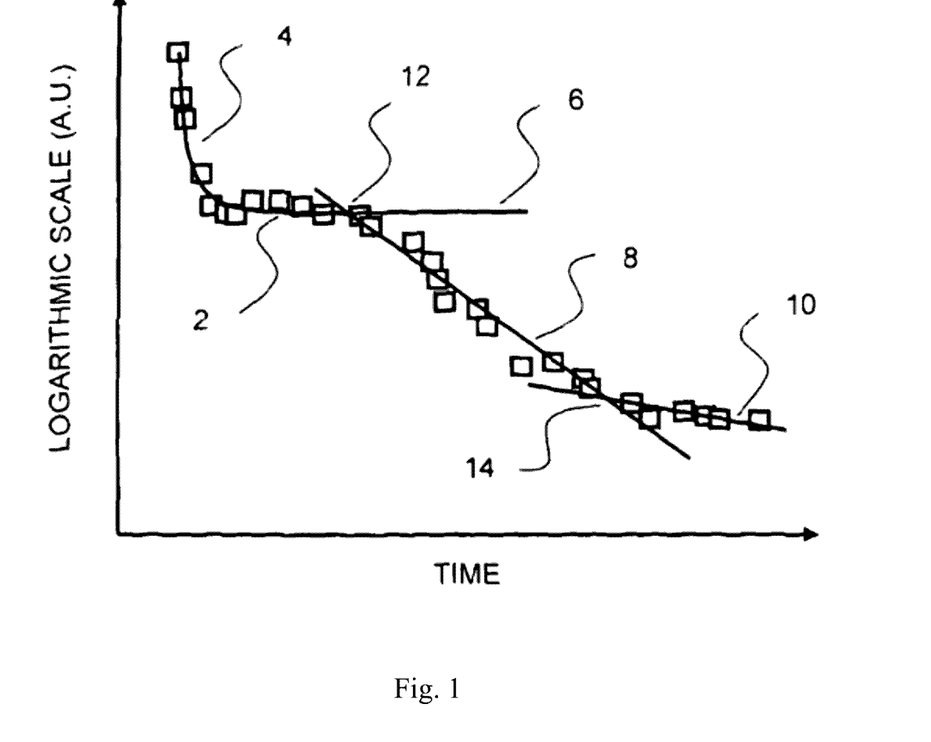
FIG. 1 shows a graph depicting a dark adaptation (DA) curve.

Following exposure of a mammalian retina to a bright light (often referred to as a bleach), a cascade of biochemical activity occurs in the retina. Recovery in sensitivity of the retina following exposure to the bleach may be regarded as slow, and might be for example of the order of 20 to 30 minutes. The recovery of the retina, or at least components thereof, may be described as having three distinct components. FIG. 1 will be used to describe and distinguish these components. FIG. 1 is a semi-log plot depicting threshold measurements measured over a period of time as perceived by a mammalian retina in the period of recovery after a bleach. Data points 2, depicted by open squares, are shown.

The three distinct components of the recovery are depicted by trend lines 4, 6, 8, 10. Changes from one component to another component, which approximately correspond to in intersection points of the aforementioned trend lines 4, 6, 8, 10 are also shown 12, 14.

The first component 4 in the recovery is dominated by cone photoreceptors, and for example may last around 8 minutes. The first component 4 may be described as exponential on the semi-log plot, and the first component has a relatively short time constant compared with the second component 8 and third component 10. The second and third components 8, 10 are dominated by rod photoreceptors.

The first component, after decaying exponentially, eventually levels out and defines what is known in the art as a cone threshold or a cone plateau 6. A transition between the cone-dominated first recovery component 4 and the rod-dominated second recovery component 8 is known as the rod-cone break 12. The second rod-dominated component 8 has a steeper (linear) gradient than the (linear) gradient of the third rod-dominated component 10. A transition point between the second component 8 and third component 10 is shown 14. It can be seen that around this transition, it may be difficult to determine whether data points are representative of the second component 8 or the third component 10.

FIG. 1 is often described as a dark adaptation curve or plot (or a sensitivity recovery curve or plot). This is because the curve shows how different components of the retina take different periods of time to recover to normal sensitivity levels after being bleached. The recovery is determined by measuring threshold levels of the perceptibility of a target presented to the user in or on an otherwise dark background, against which the sensitivity (or recovery in sensitivity) is to be assessed.

The dynamics of a dark adaptation curve are dependent on, for example, the integrated energy of the aforementioned bleach (e.g. one or more of the intensity and/or duration of the bleach). The term "bleach" is often used, because it induces a change in a photopigment contained in the retina (rhodopsin) to its colourless form.

Due to its link with age related macular degeneration (AMD) there is lots of interest in dark adaptation (DA). Historically measuring DA has posed many problems. A major problem is the duration of the testing procedure and interpretation of the resultant data.

Figure 2:
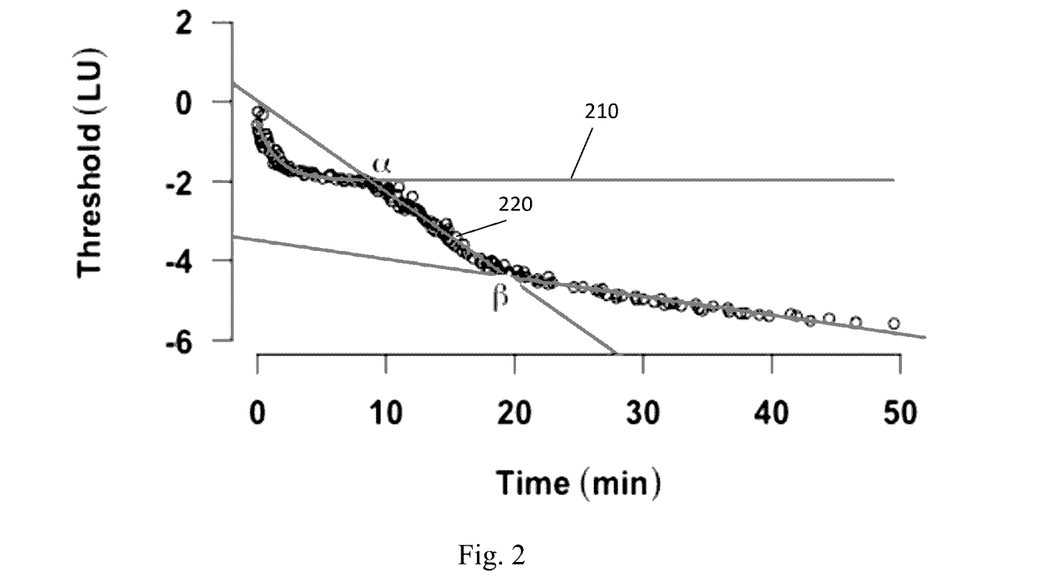
FIG. 2 shows a DA curve and carious phases.
Figure 3:
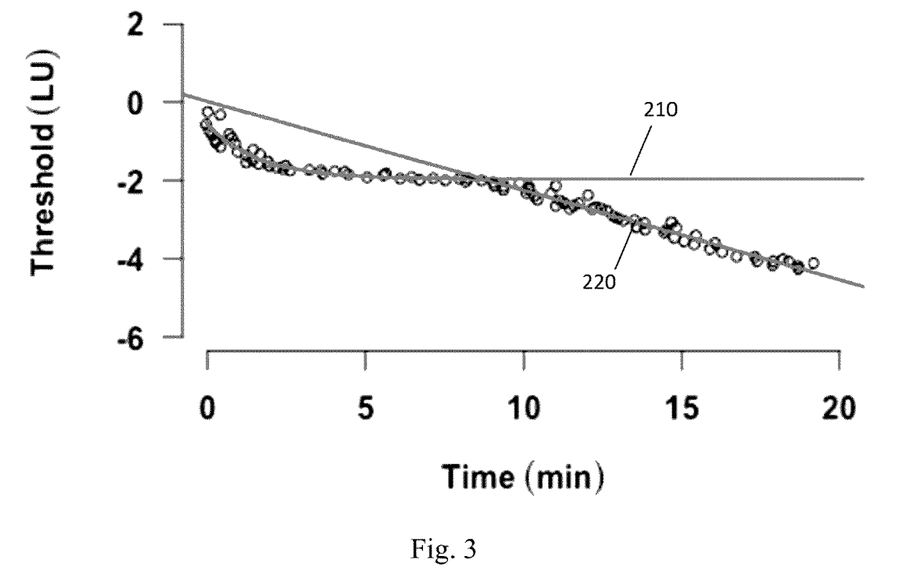
FIG. 3 shows a DA curve with an indication of S2 phase.

DA is process of recovery of sensitivity when plunged into darkness after exposure to a bright light, as described above. Threshold measurement data is plotted in terms of time, as shown in FIG. 1, and a function fitting to this data is not easily handled mathematically. Interpretation of the different phases, whether cone or rod mediated, is biologically robust. A suitable function is illustrated in FIG. 2. Characterising the function is complicated by its nonlinearities, see e.g. $\alpha$ and $\beta$ in FIG. 2. The parameters of the model are indicated in FIG. 3 which shows an exponential decay 210, due to cones, followed by a linear phase 220. The most important of these is the rate of rod recovery called S2 (lu/min), as represented by the linear phase, which represents the ability of the retina to restore photo-pigments to the rods from the outer retinal layers. It is this index that is grossly abnormal in AMD.

It is an object of embodiments of the invention to at least mitigate one or more of the problems of the prior art.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 4:
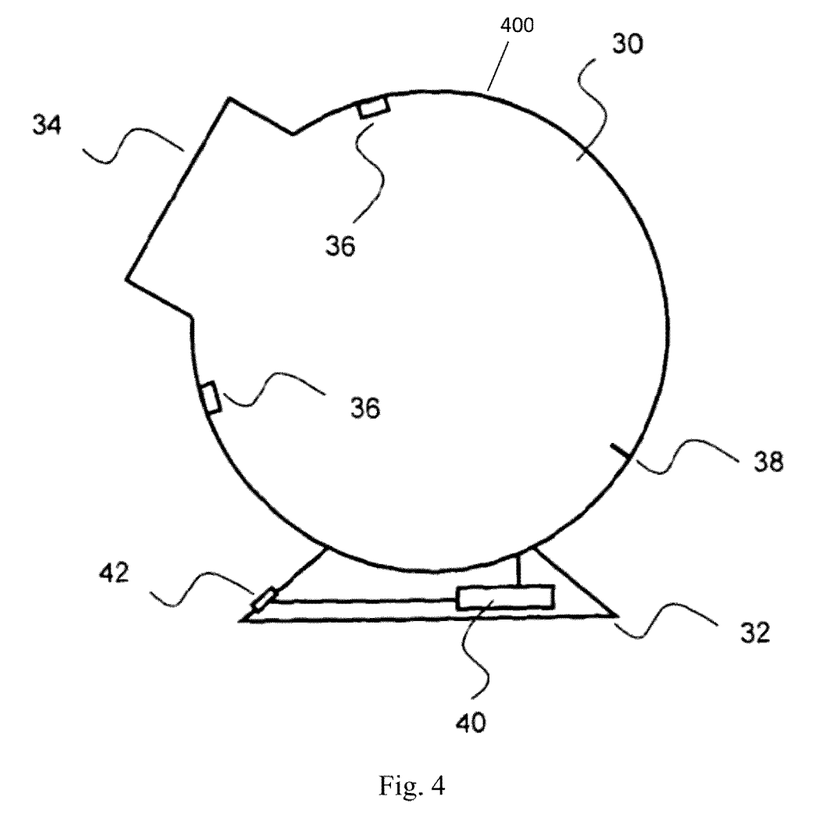
FIG. 4 shows an example measurement apparatus for measuring a property of an eye.

FIG. 4 schematically depicts a measurement apparatus 400 for measuring a property of an eye of a subject, for example, a dark adaptation (DA) curve or a sensitivity recovery. Whilst one apparatus is shown and described as an example, it will be appreciated that other types of measurement apparatus may be used with embodiments of the invention and the present invention is not restricted in this respect.

The apparatus 400 comprises a chamber 30 mounted on a stand 32. The chamber 30 may be, for example, an integrating sphere or the like. A viewing port 34 is provided which allows a subject to look inside and view at least a part of an inside of the chamber 30. The apparatus further comprises one or more light sources 36 located, in this embodiment, within the chamber 30. In other embodiments the light sources may be located outside of the chamber, and light directed from the light sources into the chamber. Referring back to FIG. 4, the light sources 36 are arranged to provide (in no particular order, but instead at an appropriate time, as will be explained) a bleaching light, a substantially red background light, and a substantially green target light. In another embodiment, the light sources may (e.g. additionally) provide a substantially green background light and a substantially red target light. Located within the chamber 30 is a fixation point 38 which may be an object or mark or the like provided in the chamber 30. The aforementioned target light described generally above is presented to the user with a particular angular relationship relative to the fixation point 38, as will be described in more detail below.

Located within the stand is a control arrangement 40 for controlling the apparatus. The control arrangement 40 may be or comprise a computer or other form of processor or the like. In another embodiment (not shown), the control arrangement may be located outside of, or away from, the stand, and may be in wired or wireless connection with the lights and the like. Referring back to the Figure, the control arrangement 40 is configured to control the apparatus to implement the method according to an embodiment of the present invention, described above and in more detail below.

An indication device 42, for example in the form of a button or the like, is also provided, so that a subject can provide an input to the apparatus, for example indicating when a target light, or the perception of modulation (i.e. flicker) thereof, is visible.

In the embodiment shown in FIG. 4, the lights 36 may be used to provide an appropriate target and an appropriate background to that target, relative to the fixation point 38. For instance, the lights 36 may project the target onto an internal surface of the chamber 30 relative to the fixation point 38. In another embodiment, shown in FIG. 4, the chamber 30 may additionally comprise a screen 50 onto which the target and/or background light may be projected. The light may be projected from in front of the machine by the lights 36 described above, or alternatively or additionally by lights 52 residing behind the screen 50.

In other arrangements, not shown, there may be no need or no requirement to project the background light or a target light. Instead, one or both lights may be provided by a subject viewing the light source itself, as opposed to lights emitted from that light source. For example, a screen may be provided such as for example an organic light emitting diode screen, or a liquid crystal display screen, via which the target may be provided.

In any embodiment, the background light and target light are superimposable, so that the target light may be presented on the background light, a contrast or relative luminance between the target light and the background light being variable by varying the luminance (for example) of the target light.

Figure 5:
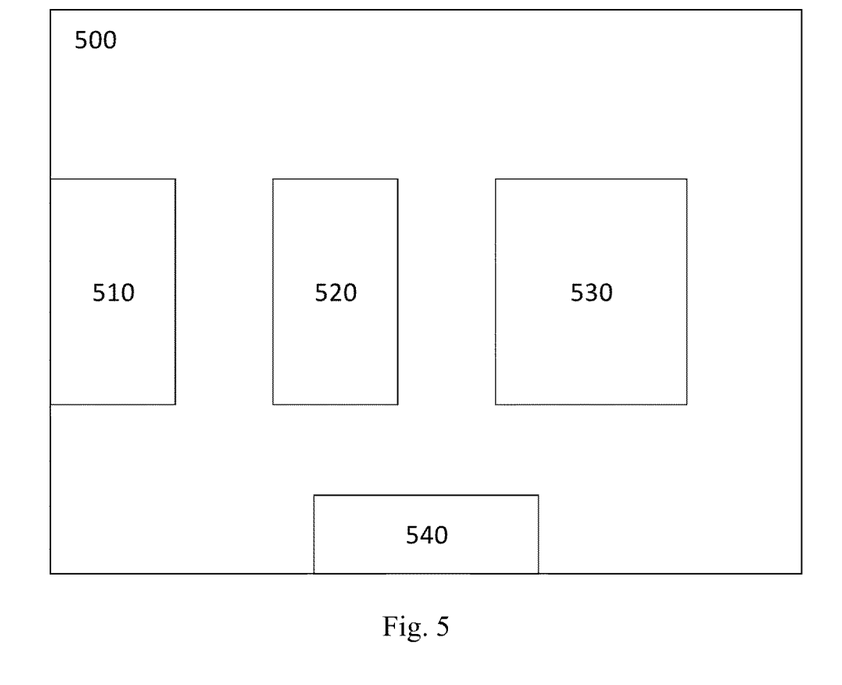
FIG. 5 illustrates an apparatus 500 according to an embodiment of the invention.

Using the apparatus 400 of FIG. 4, or any other suitable apparatus, threshold data is provided over a period of time. The threshold data comprises a series of threshold measurement, each threshold measurement being made at a respective point in time over a measurement period. Each threshold measurement may be made at an interval of up to 1 minute. In some embodiments, the interval is less than 30 second. In some embodiments, the interval is between 10 and 20 seconds. In some embodiments the interval is 15 second. As produced, each threshold measurement may be provided, substantially in real time, to an apparatus 500 according to an embodiment of the invention as shown in FIG. 5. Conventionally it is required for a subject to use the apparatus of FIG. 4, or similar, for a measurement period of upwards of 30 minutes, such as for an hour, then to subsequently process the threshold data to analysis. Such long measurement periods are uncomfortable for the subject. It has been discovered by the present inventors that the measurement period may be substantially reduced.

For example, it is possible using embodiments of the invention to determine an indication of the rate of rod recovery, such as S2, within 10 minutes, for example. It will be recalled that the rate of rod recovery may correspond to the linear portion illustrated in FIGS. 1-3.

FIG. 5 illustrates an apparatus 500 according to an embodiment of the invention. The apparatus 500 comprises an input unit 510, a memory unit 520, a processing unit 530 and an output unit 540.

The input unit 510 is an interface for receiving threshold data. The input unit 510 may provide an interface to the apparatus 400 illustrated in FIG. 4. The input unit 510 may be arranged to receive an electrical signal indicative of the threshold data. In some embodiments, the input unit 510 may be a network interface for receiving the threshold data.

The output unit 540 is arranged to output an indication of one or more values determined by the processing unit based on the threshold data stored in the memory unit, as will be explained.

The processing unit 530 comprises one or more electronic processing devices or processors. The processing unit may execute computer-readable instructions which are stored in the memory unit 520. The computer-readable instructions may form computer software according to an embodiment of the invention.

The memory unit 520 is one or more memory devices for storing data therein. The memory unit 520 stores at least first and second dark adaptation models. The first model is associated with a first dark adaptation mechanism and the second model is associated with a plurality of dark adaption mechanisms. The second model may be associated with the first dark adaption mechanism and a second dark adaptation mechanism. In some embodiments, the memory unit 520 stores one or more further models.

The first model may be of the form:

$$CT + OffC \cdot \exp^{\left(\frac{-time}{\tau_c}\right)} \qquad \text{Equation 1}$$

The second model may be of the form:

$$CT + OffC \cdot \exp^{\left(\frac{-time}{\tau_c}\right)} + Tr(\alpha) \cdot (S2 \cdot (time - \alpha)) \qquad \text{Equation 2}$$

In the first and second models:
CT is a cone threshold, which may have units of LU;
OffC is an offset from the cone threshold to a predetermined value, such as time=0;
$\tau_c$ is a time constant indicative of a speed of threshold recovery in a cone phase;
α is indicative of a transition time;
S2 is a rate of recovery, which may have units of LU/min; and time is a current time.

In some embodiments a further, third, model may be of the form:

$$CT + OffC \cdot \exp^{\left(\frac{-time}{\tau_c}\right)} + \\ Tr(\alpha) \cdot (S2 \cdot (time - \alpha)) + Tr(\beta)((S2 + S3) \cdot (time - \beta)) \qquad \text{Equation 3}$$

Where:
S3 is a rate of recovery, which may have units of LU/min;
β is indicative of a transition time.

The first model is associated with the first dark adaptation mechanism. The second model is associated with the first dark adaption mechanism and a second dark adaptation mechanism. Other than the first model, each dark adaptation model may include prior dark adaptation mechanism(s) with at least one transition function. For example, the second dark adaptation model may include the first dark adaptation model with a transition function there-between, as will be explained.

The first model may model cone recovery. The first model may model an early phase of a DA curve. The first model may represent the trend 210 in FIGS. 2 and 3.

The second model may model cone and rod recovery. The second model may correspond to the first model and also include rod recovery. A transition function may link the cone and rod recovery models. A transition point between the two models is associated with parameter α. The second model is represented by a combination of the trends 210, 220 shown in FIGS. 2 and 3.

As can be appreciated from the above, the first and second models, and in some embodiments the third model, are smooth or continuous. Advantageously the use of such smooth or continuous functions allows for differentiation. In this way analytic methods may be used to determine a confidence interval associated with each model. In some embodiments the smooth or continuous function is a logistic function. In some embodiments the smooth or continuous function is a Weibull, arc tan or Hill function. The smooth or continuous function may be one having a limited range of asymptotic values.

The above second and third models include one or more transition functions Tr( ) with a respective parameter, either α or β, respectively. Each transition function is associated with a change between respective regions of dark adaptation.

Figure 6:
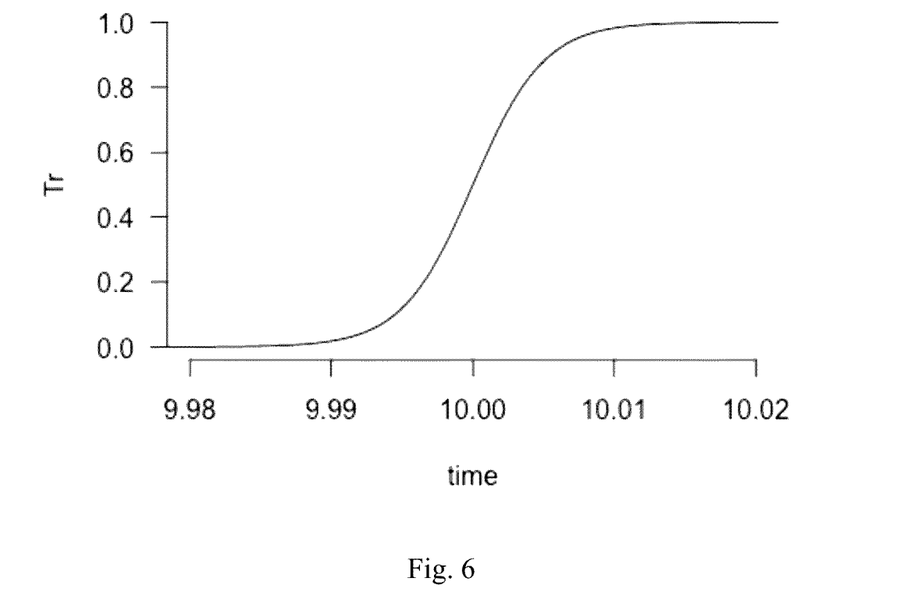
FIG. 6 is a graph depicting a transition function according to an embodiment of the invention.

It can be appreciated from FIG. 6, which shows a transition function Tr(α) where α=10. It can be appreciated that the function is continuous and takes a value of between 0 and 1, switching relatively quickly from values at respective ends of the spectrum i.e. 0 or 1.

Any smooth function that asymptotically takes values between zero and one may be used for the transition function.

In some embodiments, the transition function, Tr(α) where a may be replaced with β etc, is:

$$Tr(\alpha) = \frac{1}{\exp(-k*(\text{time}-\alpha))} \quad \text{Equation 4}$$

Where:
k is a time constant of a transition associated with the function; k may be set at a constant value or can be a variable associated with a model.

Confidence Interval Calculation

Each model may be fitted to the received threshold data by adjusting the parameters of the respective model to obtain a best fit to the received threshold data. That is, until each estimated threshold measurement from the model is as close as possible to the respective threshold measurement from the received threshold data. A difference between the estimated threshold measurement and the threshold measurement in the threshold data is a residual. A sum of squared residuals for the threshold data may be reduced to a minimum by the fitting.

Figure 7:
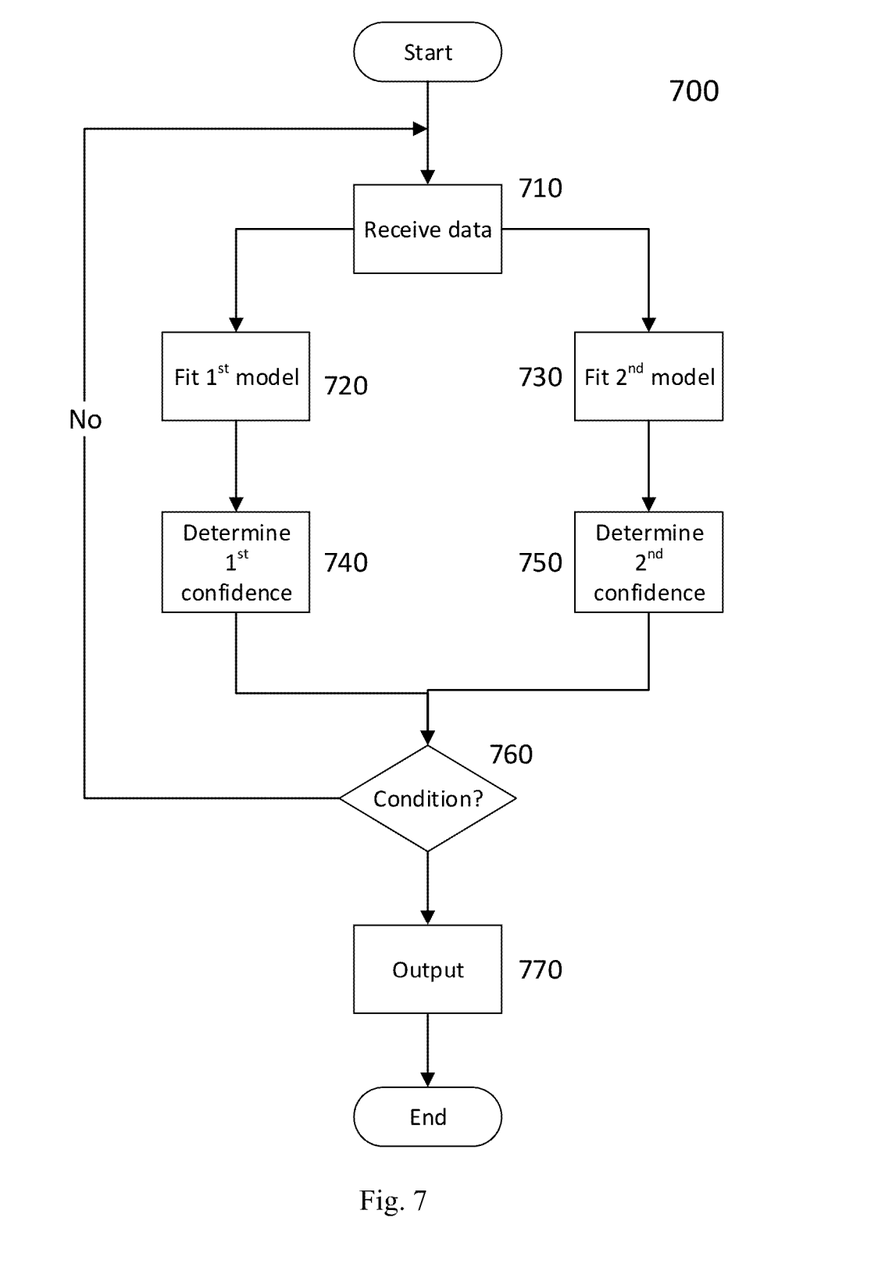
FIG. 7 is a method according to an embodiment of the invention.

Embodiments of the method utilise the sum of squared residuals, and determine an estimate of a variance of the residuals taking account of the number of parameters of the model and the number of threshold measurements, i.e. data points. The variance is combined with a covariance matrix of the parameters. In this way a confidence interval for each parameter may be determined, as explained further below in connection with step 740.

FIG. 7 illustrates a method 700 according to an embodiment of the invention. The method 700 is a method of determining a parameter indicative of dark adaptation of an eye of a subject. The method 700 may be performed by the apparatus illustrated in FIG. 5. The method 700 may be performed by the processing unit 530. The method may be iteratively performed i.e. at least some steps of the method 700 may be repeated until one or more predetermined conditions are met, as will be explained.

In step 710 threshold data is received. In each iteration of step 710 the threshold data comprises one or more threshold measurements. The accumulated i.e. total received number of threshold measurements increases for each repetition of step 710. For example, in some embodiments, in a first iteration of step 710 the threshold data may comprise a first threshold measurement. The, or each, threshold measurement is at a respective time. The first threshold measurement may be at time=1, although other intervals may be used. For a second iteration of step 710 the threshold data may comprise one or more threshold measurements i.e. more than one threshold measurement may be received in step 710. In a further example, in the second iteration of step 710 a second threshold measurement may be received. The second threshold measurement may be at a time=2. In each iteration of step 710 the threshold data is stored in the memory unit 520. Thus as the method 700 progresses, a volume of threshold data in the memory unit 520 increases.

The method progresses to steps 720 and 730 in the illustrated example. It will be appreciated that, whilst these steps may be performed at least partly in parallel, this is not necessary. For example, step 720 may be performed before or after step 730.

In each of steps 720 and 730 a fitting processes is performed. The fitting process is performed to fit a respective model to the received threshold data in each of steps 720 and 730. In step 720 the first model, such as described above, is fitted to the received threshold data. In step 730 the second model, such as described above, is fitted to the received threshold data. Each of steps 720 and 730 comprises determining a respective set of parameters associated with the model which fits the model to the received threshold data. The method 700 may comprise one or more further steps in which a fitting process of the received threshold data is performed to a further model, such as the third model.

In each of steps 740 and 750 a respective confidence is determined in dependence on the respective model associated with the set of parameters determined in each of steps 720, 730, respectively. The confidence may be a confidence interval associated with each of the first and second models.

Step 740 will be described as an example. It will be appreciated that equivalent steps may be performed for step 750 and any further models used by the method 700.

In step 740 a partial derivative of the respective model is determined with respect to each parameter. It will be appreciated in some embodiments that the partial derivates of the model are determined apriori. The partial derivatives are evaluated for each parameter estimate using the time associated with each of the threshold data measurements. Using linear algebra a covariance matrix is determined that allocates the variance of the residuals across the parameters of the respective model.

A diagonal of the determined covariance matrix provides a variance of each parameter estimate and the subsequent confidence intervals using a Fisher or F distribution. As will be appreciated by the skilled person the F distribution is a continuous probability distribution used in the analysis of variance.

In step 760 it is determined whether one or more predetermined conditions are met. In some embodiments, the one or more conditions whether a confidence interval associated with one or more of the models is at least a predetermined value. In some embodiments, it is determined in step 760 whether a confidence interval associated with the second model is at least a predetermined value. If the one or more conditions are not met in step 760, the method returns to step 710. Steps 710-750 are then repeated in a further iteration.

If, however, the one or more predetermined conditions are met in step 760 the method moves to step 770. In step 770 an indication of one or more parameters associated with at least one model are output. In particular, a value of S2 is output. However it can also be appreciated that other values determined as part of the model may be output, as shown below.

An example output from the method 700 in step 760 is given:

| ## | L Bound | Estimate | U Bound |
| --- | --- | --- | --- |
| ## CT | −2.075 | −1.967 | −1.858 |
| ## CC | 1.126 | 1.390 | 1.655 |
| ## Tau | 0.912 | 1.609 | 2.306 |
| ## S2 | −0.252 | −0.228 | −0.204 |
| ## Alpha | 7.940 | 8.704 | 9.467 |
| ## *S3* | 0.155 | 0.181 | 0.207 |
| ## Beta | 18.296 | 19.425 | 20.554 |

[1] "The analytic time is 0.0129 seconds"

As noted above, a time taken to determine values by a method according to an embodiment of the invention is 0.0129 seconds. Advantageously this computation time is much shorter than for some prior art methods. For example, a comparative method known as a 'bootstrap' method was performed which took 2.14 seconds and produced comparable values. Furthermore, by determining one or more values indicative of dark adaptation as testing of the eye progresses i.e. whilst threshold data is produced, and determination of a confidence associated with the one or more values, a duration of the test to which the subject is subjected to can be reduced. That is, the test can be terminated when the confidence is sufficiently high.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A computer-implemented method of determining a parameter indicative of dark adaptation of an eye, comprising:
    receiving threshold data from a dark adaptometer indicative of a perception threshold of the eye;
    fitting first and second models to the threshold data, wherein the first model is associated with a first dark adaptation mechanism and the second model is associated with the first dark adaption mechanism and a second dark adaptation mechanism;
    determining a confidence associated with the fitting of each of the first and second models to the received threshold data;
    iteratively repeating the steps of receiving the threshold data and fitting the first and second models in dependence on the determined confidence; and
    outputting an indication of one or more parameters indicative of dark adaptation of an eye associated with one or both of the first and second models.

2. The method of claim 1, wherein determining the confidence comprises:
    determining a variance of each of the first and second models to the received threshold data;
    determining a covariance matrix based on a partial derivative associated with each of the first and second models;
    determining the confidence for each of the first and second models in dependence on the covariance matrix.

3. The method of claim 1, wherein the steps of receiving the threshold data and fitting the first and second model are repeated until the confidence is at least a predetermined confidence value.

4. The method of claim 1, wherein the one or more parameters comprise a parameter indicative of a rate of rod recovery.

5. The method of claim 4, wherein the parameter indicative of the rate of rod recovery is an S2 parameter.

6. The method of claim 1, wherein the first model is:

$$CT + OffC \cdot \exp\left(\frac{-time}{\tau_c}\right)$$

wherein

CT is a cone threshold, which may have units of LU, OffC is an offset from the cone threshold to a predetermined value, $\tau_c$ is a time constant indicative of a speed of threshold recovery in a cone phase, $\alpha$ is indicative of a transition time, and time is a current time.

7. The method of claim 1, wherein the second model is:

$$CT + OffC \cdot \exp\left(\frac{-time}{\tau_c}\right) + Tr(\alpha) \cdot (S2 \cdot (time - \alpha)) + Tr(\beta)((S2 + S3) \cdot (time - \beta))$$

CT is a cone threshold, which may have units of LU;

OffC is an offset from the cone threshold to a predetermined value, such as time=0;

$\tau_c$ is a time constant indicative of a speed of threshold recovery in a cone phase;

$\alpha$ is indicative of a transition time;

S2 is a rate of recovery, which may have units of LU/min; and time is a current time.

8. The method of claim 1, wherein the fitting the first and second models to the threshold data comprises determining one or more parameters associated with each model to determine a minimum sum of squared residual values.

9. An apparatus for determining a parameter indicative of dark adaptation of an eye, comprising:

an interface arranged to receive an electrical signal indicative of threshold data from a dark adaptometer indicative of a perception threshold of the eye;

a memory for storing the received threshold data;

a processor arranged to, in use:

fit first and second models to the threshold data, wherein the first model is associated with a first dark adaptation mechanism and the second model is associated with the first dark adaption mechanism and a second dark adaptation mechanism;

determine a confidence associated with the fitting of each of the first and second models to the received threshold data;

iteratively repeat the steps of receiving the threshold data and fitting the first and second models in dependence on the determined confidence; and output an indication of one or more parameters indicative of dark adaptation of an eye associated with one or both of the first and second models.

10. A system, comprising:

a dark adaptometer comprising a plurality of light sources, the dark adaptometer being arranged to measure a property of an eye of a subject and to provide threshold data to the interface of an apparatus according to claim 9.

11. Computer software stored on a non-transitory computer-readable medium which, when executed by a computer is arranged to cause the computer to perform a method according to claim 1.

* * * * *